United States Patent
Parramon et al.

(10) Patent No.: US 9,855,438 B2
(45) Date of Patent: *Jan. 2, 2018

(54) BATTERY MANAGEMENT FOR AN IMPLANTABLE MEDICAL DEVICE

(71) Applicant: Boston Scientific Neuromodulation Corporation, Valencia, CA (US)

(72) Inventors: Jordi Parramon, Valencia, CA (US); Goran N. Marnfeldt, Valencia, CA (US); Robert Ozawa, Woodland Hills, CA (US); Emanuel Feldman, Simi Valley, CA (US); Dave Peterson, Saugus, CA (US); Yuping He, Northridge, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/182,367

(22) Filed: Jun. 14, 2016

(65) Prior Publication Data

US 2016/0287886 A1    Oct. 6, 2016

Related U.S. Application Data

(62) Division of application No. 13/489,770, filed on Jun. 6, 2012, now Pat. No. 9,393,433.

(Continued)

(51) Int. Cl.
*A61N 1/378* (2006.01)
*A61N 1/08* (2006.01)

(52) U.S. Cl.
CPC ............ *A61N 1/3787* (2013.01); *A61N 1/08* (2013.01)

(58) Field of Classification Search
CPC ...... A61N 1/08; A61N 1/36142; A61N 1/378; A61N 1/3787; A61B 2560/0204;
(Continued)

(56) References Cited

U.S. PATENT DOCUMENTS

| 3,522,811 A | 8/1970 | Wingrove et al. |
| 3,746,006 A * | 7/1973 | Thaler .................... A61N 1/362 327/172 |

(Continued)

FOREIGN PATENT DOCUMENTS

| JP | 06-031003 A | 2/1994 |
| WO | 2005/000399 A1 | 1/2005 |

OTHER PUBLICATIONS

Pao-Lo, Liu. "Series and Parallel Combinations." University of Buffalo Electrical Engineering Department. Web. Apr. 12, 2017. <http://www.ee.buffalo.edu/faculty/paololiu/edtech/roaldi/References/sp.htm>.*

(Continued)

*Primary Examiner* — Allen Porter, Jr.
(74) *Attorney, Agent, or Firm* — Lewis, Reese & Nesmith, PLLC (57) ABSTRACT

Battery management circuitry for an implantable medical device such as an implantable neurostimulator is described. The circuitry has a T-shape with respect to the battery terminal, with charging circuitry coupled between rectifier circuitry and the battery terminal on one side of the T, and load isolation circuitry coupled between the load and the battery terminal on the other side. The load isolation circuitry can comprise two switches wired in parallel. An undervoltage fault condition opens both switches to isolate the battery terminal from the load to prevent further dissipation of the battery. Other fault conditions will open only one the switches leaving the other closed to allow for reduced power to the load to continue implant operations (Continued)

albeit at safer low-power levels. The battery management circuitry can be fixed in a particular location on an integrated circuit which also includes for example the stimulation circuitry for the electrodes.

20 Claims, 9 Drawing Sheets

Related U.S. Application Data (60) Provisional application No. 61/509,701, filed on Jul. 20, 2011.

(58) Field of Classification Search
CPC ... A61B 2560/0214; A61B 2560/0219; H01M 10/44
USPC .......................................................... 607/61
See application file for complete search history.

(56) References Cited

U.S. PATENT DOCUMENTS

| | | | |
|---|---|---|---|
| 3,867,950 A | 2/1975 | Fischell | |
| 3,888,260 A | 6/1975 | Fischell | |
| 3,942,535 A | 3/1976 | Schulman | |
| 4,082,097 A | 4/1978 | Mann et al. | |
| 4,592,359 A | 6/1986 | Galbraith | |
| 4,947,844 A | 8/1990 | McDermott | |
| 5,369,351 A * | 11/1994 | Adams | A61N 1/378 320/121 |
| 5,391,191 A * | 2/1995 | Holmstrom | A61N 1/365 607/28 |
| 5,702,431 A | 12/1997 | Wang et al. | |
| 5,713,939 A | 2/1998 | Nedungadi et al. | |
| 5,733,313 A | 3/1998 | Barreras, Sr. et al. | |
| 5,869,970 A | 2/1999 | Palm et al. | |
| 5,925,068 A | 7/1999 | Kroll | |
| 6,233,483 B1 * | 5/2001 | Causey, III | A61N 1/3906 607/5 |
| 6,331,763 B1 | 12/2001 | Thomas | |
| 6,507,173 B1 | 1/2003 | Spiridon et al. | |
| 6,553,263 B1 | 4/2003 | Meadows et al. | |
| 6,583,603 B1 | 6/2003 | Baldwin | |
| 6,757,566 B2 | 6/2004 | Weiner et al. | |
| 6,778,856 B2 | 8/2004 | Connelly et al. | |
| 6,894,456 B2 | 5/2005 | Tsukamoto et al. | |
| 7,177,691 B2 | 2/2007 | Meadows et al. | |
| 7,184,836 B1 | 2/2007 | Meadows et al. | |
| 7,212,110 B1 | 5/2007 | Martin et al. | |
| 7,221,977 B1 * | 5/2007 | Weaver | A61N 1/3708 320/136 |
| 7,248,929 B2 | 7/2007 | Meadows et al. | |
| 7,295,878 B1 | 11/2007 | Meadows et al. | |
| 7,428,438 B2 | 9/2008 | Parramon et al. | |
| 7,565,204 B2 | 7/2009 | Matei | |
| 7,962,222 B2 | 6/2011 | He et al. | |
| 8,026,637 B2 * | 9/2011 | Seligman | A61N 1/378 307/48 |
| 9,209,632 B2 | 12/2015 | Kadirvel, III | |
| 9,325,179 B1 * | 4/2016 | Voytenko | H02J 7/0024 |
| 2002/0045921 A1 | 4/2002 | Wolinsky et al. | |
| 2002/0062137 A1 * | 5/2002 | Digby | A61N 1/08 607/5 |
| 2003/0114899 A1 * | 6/2003 | Woods | A61N 1/36071 607/60 |
| 2005/0043594 A1 | 2/2005 | Dismoor et al. | |
| 2005/0052154 A1 | 3/2005 | Kavounas | |
| 2005/0131495 A1 | 6/2005 | Parramon et al. | |
| 2006/0265027 A1 | 11/2006 | Vaingast et al. | |
| 2007/0038250 A1 | 2/2007 | He et al. | |
| 2007/0129768 A1 | 6/2007 | He et al. | |
| 2007/0203528 A1 | 8/2007 | Vernon | |
| 2008/0094042 A1 | 4/2008 | Ferrario | |
| 2009/0076336 A1 * | 3/2009 | Mazar | A61B 5/0402 600/300 |
| 2010/0305662 A1 | 12/2010 | Ozawa et al. | |
| 2011/0006969 A1 | 1/2011 | Batikoff et al. | |
| 2011/0112610 A1 * | 5/2011 | Rahman | A61N 1/3718 607/60 |
| 2011/0121777 A1 | 5/2011 | Carbunaru et al. | |
| 2011/0276110 A1 | 11/2011 | Whitehurst et al. | |
| 2012/0010476 A1 * | 1/2012 | Chambers | A61N 1/36032 600/301 |

OTHER PUBLICATIONS

U.S. Appl. No. 11/215,946, filed Aug. 30, 2005, Yan.
Data Sheet for Motorola Device No. MC33349, "Lithium Battery Protection Circuit for One Cell Battery Packs" (May 2000).
International Search Report and Written Opinion regarding corresponding PCT application No. PCT/US2012/041551, dated Aug. 3, 2012.
Communication pursuant to Article 94(3) EPC regarding corresponding European Patent Application No. 16167789.3, dated Jul. 31, 2017.

* cited by examiner

BATTERY MANAGEMENT FOR AN IMPLANTABLE MEDICAL DEVICE

CROSS REFERENCE TO RELATED APPLICATIONS

This application is a divisional of U.S. patent application Ser. No. 13/489,770, filed Jun. 6, 2012 (now allowed), which is a non-provisional application of U.S. patent application Ser. No. 61/509,701, filed Jul. 20, 2011. Priority is claimed to these applications, and they are incorporated herein by reference in their entireties.

FIELD OF THE INVENTION

This application relates to the field of implantable medical devices, and in particular to management circuitry for an implantable medical device having a battery.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable neurostimulator.

Figures 1A, 1B:
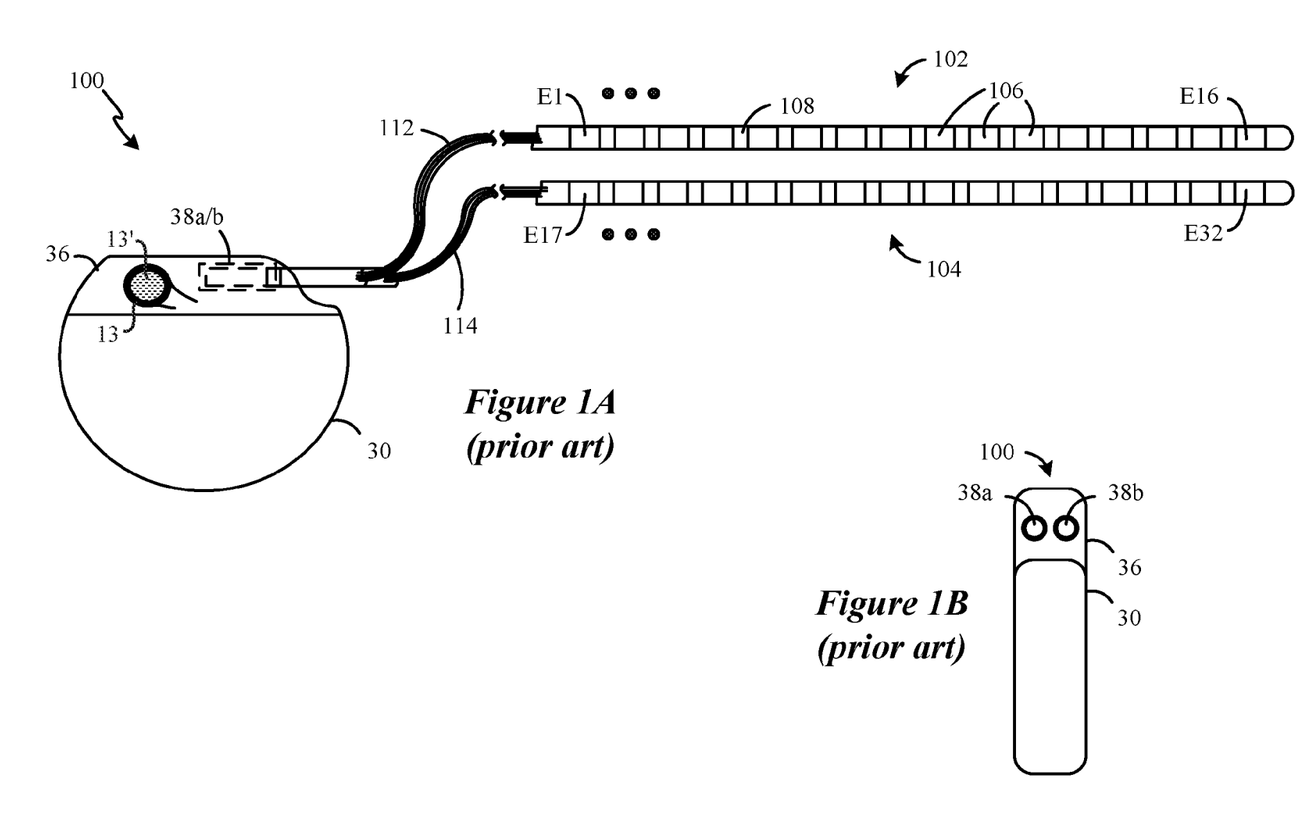
FIGS. 1A and 1B show an implantable pulse generator (IPG), and the manner in which an electrode array is coupled to the IPG in accordance with the prior art.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are sixteen electrodes on array 102, labeled E1-E16, and sixteen electrodes on array 104, labeled E17-E32, although the number of arrays and electrodes is application specific and therefore can vary. The arrays 102, 104 couple to the IPG 100 using lead connectors 38a and 38b, which are fixed in a non-conductive header material 36, which can comprise an epoxy for example. In another example, the IPG 100 can include four lead connectors supporting four electrode arrays each having eight electrodes.

Figure 2:
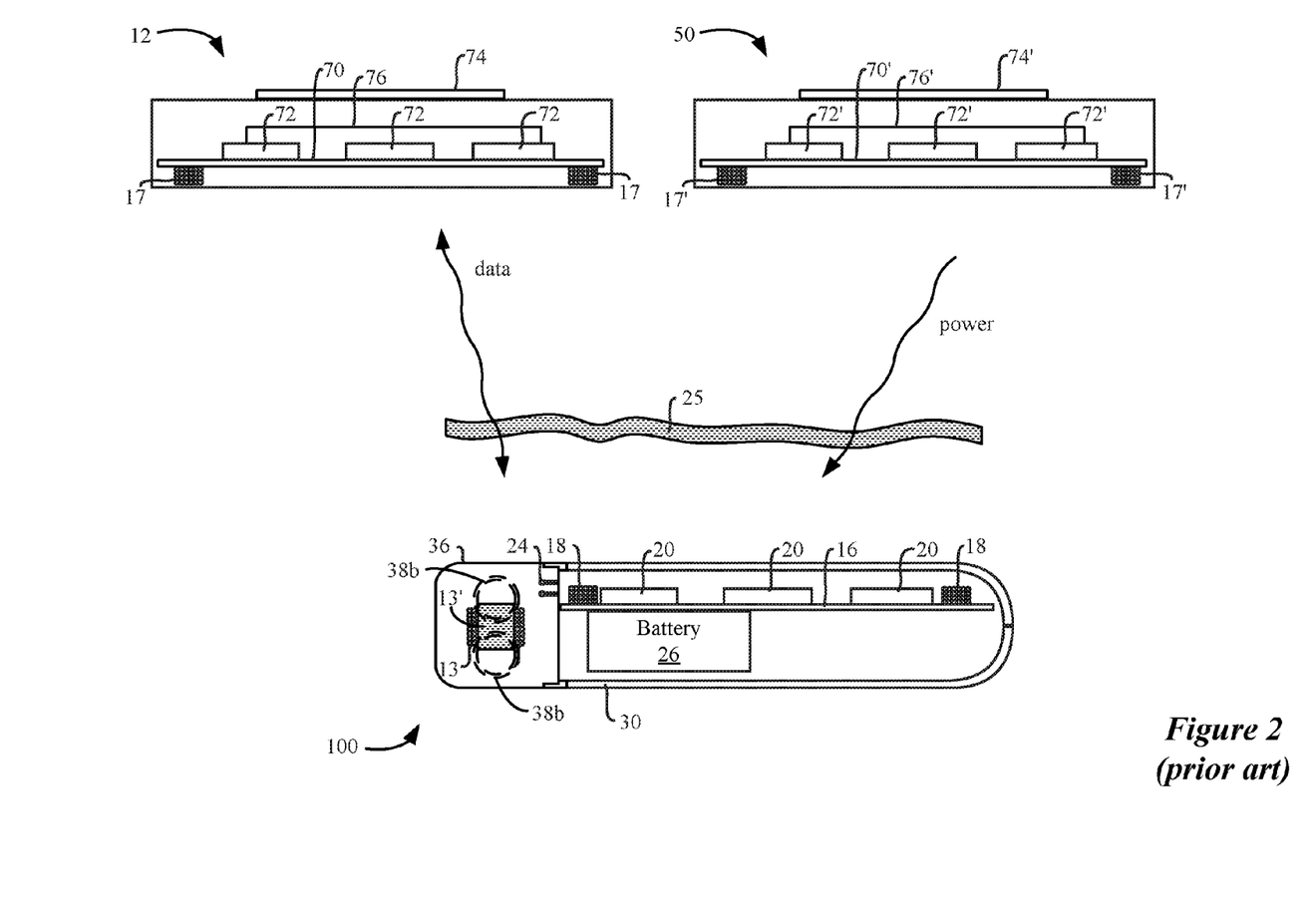
FIG. 2 shows an IPG, an external controller, and an external charger in accordance with the prior art.

As shown in FIG. 2, the IPG 100 typically includes an electronic substrate assembly including a printed circuit board (PCB) 16, along with various electronic components 20, such as microprocessors, integrated circuits, and capacitors mounted to the PCB 16. Depending on the design and the type of batteries used, two coils (more generally, antennas) may be present in the IPG 100: a telemetry coil 13 used to transmit/receive data to/from an external controller 12; and a charging coil 18 for charging or recharging the IPG's battery 26 using an external charger 50. The telemetry coil 13 is shown mounted within the header 36 of the IPG 100 as shown, and may be wrapped around a ferrite core 13'. However, the telemetry coil 13 may also be placed inside the case 30. See, e.g., U.S. Patent Publication 2011/0112610, which is incorporated herein by reference.

As just noted, an external controller 12, such as a hand-held programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

The external charger 50, also typically a hand-held device, is used to wirelessly convey power to the IPG 100, which power can be used to recharge the IPG's battery 26. The transfer of power from the external charger 50 is enabled by a coil (antenna) 17', which generates a magnetic charging field. The external charger 50 is depicted as having a similar construction to the external controller 12, but in reality they will differ in accordance with their functionalities as one skilled in the art will appreciate.

The IPG 100 can also communicate data back to the external charger 50 during charging by modulating the impedance of the charging coil 18. This change in impedance is reflected back to coil 17' in the external charger 50, which demodulates the reflection to recover the transmitted data. This means of transmitting data from the IPG 100 to the external charger 50 is known as Load Shift Keying (LSK), and is useful to communicate data relevant during charging of the battery 26 in the IPG 100, such as whether charging is complete and the external charger can cease. LSK communication from an IPG 100 to an external charger is discussed further in U.S. Patent Application Publication 2010/0179618 and U.S. Pat. No. 8,577,474.

Wireless data telemetry and power transfer between the external devices 12 and 50 and the IPG 100 takes place via inductive coupling, and specifically inductive coupling. To implement such functionality, both the IPG 100 and the external devices 12 and 50 have coils which act together as a pair. In case of the external controller 12, the relevant pair of coils comprises coil 17 from the controller and coil 13 from the IPG 100. In case of the external charger 50, the relevant pair of coils comprises coil 17' from the charger and coil 18 from the IPG 100. As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

This disclosure is directed to improved battery management circuitry for an implantable medical device and related battery management schemes.

DETAILED DESCRIPTION

Figure 3:
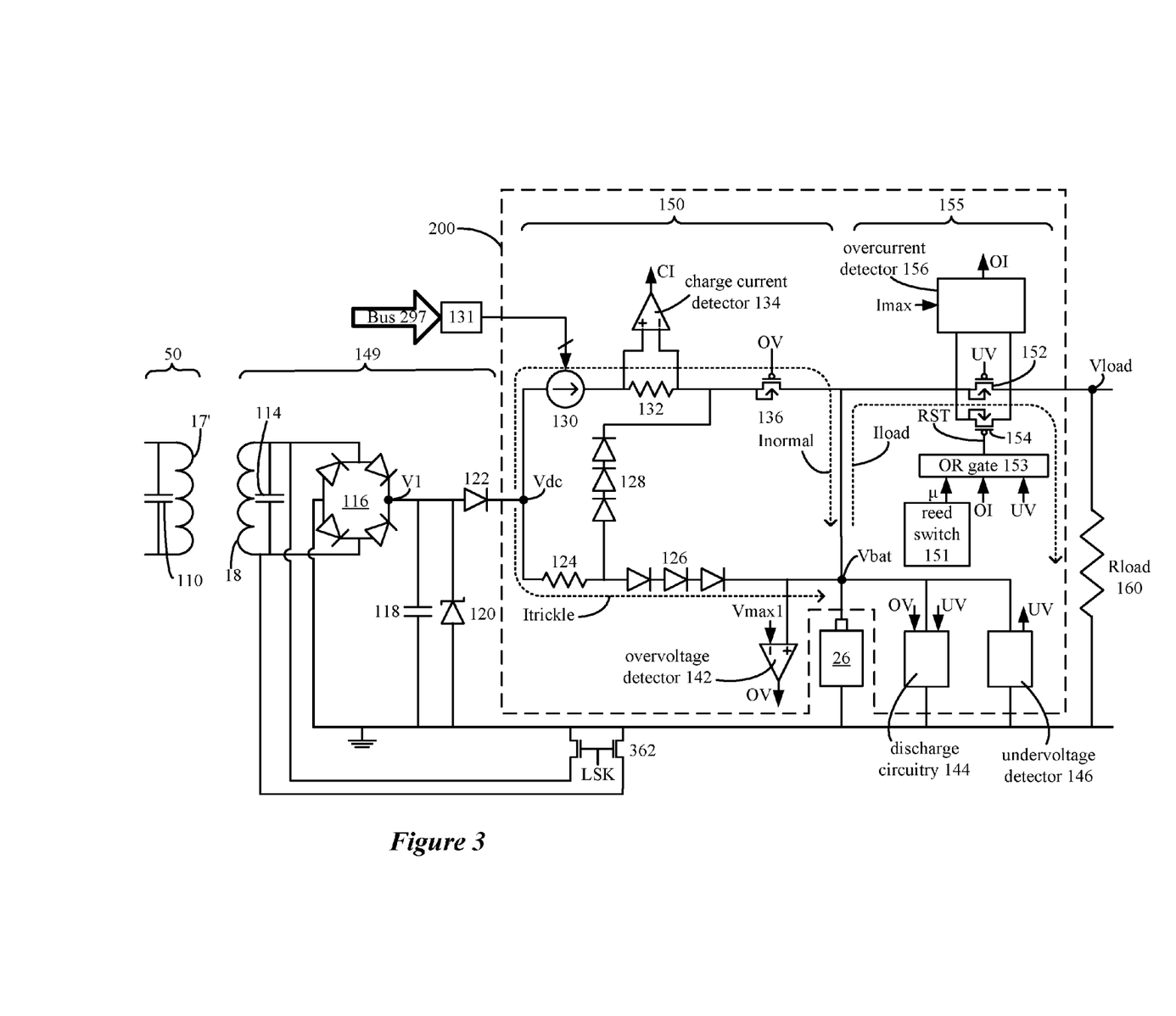
FIG. 3 shows improved battery management circuitry for an IPG.

FIG. 3 shows improved battery management circuitry 200 for an implantable medical device such as the IPG 100 discussed in the Background. The battery management circuitry 200 comprises charging circuitry 150 for generating a controlled current for charging the battery 26, and load isolation circuitry 155 which can controllably connect or disconnect the battery 26 from the load 160 that the battery 26 powers during normal operation of the IPG 100. As shown, the battery management circuitry 200 has a T-shaped topology between the charging circuitry 150, the load isolation circuitry, and the battery, such that the charging circuitry 150 intervenes between front end circuitry 149 (discussed below) and the positive terminal (Vbat) of the battery 26, and the isolation circuitry 155 intervenes between the positive terminal of the battery 26 and the load 160. Various circuits 134, 142, 144, 146, and 156 are used to monitor and control the charging circuitry 150 and the isolation circuitry 155, as will be explained in further detail later.

A capacitor 110 in the external charger 50 is coupled to its coil 17' to provide an L-C resonant or "tank" circuit for producing an AC magnetic charging field. The magnetic charging field induces a current in coil 18 in the IPG 100, which coil 18 is likewise coupled with a capacitor 114 to form a tank circuit. The AC voltage produced by the IPG's tank circuit 18/114 is converted to a first DC voltage V1 by a standard full-wave rectifier circuit 116, which V1 is filtered via capacitor 118. A Zener diode 120 keeps V1 clamped to a safe level of perhaps 5.5 Volts or so, which level is chosen to be well below the maximum ratings for the semiconductor processes and design rules used.

V1 passes through a diode 122 to produce a second DC voltage, Vdc. The diode 122 is intended to prevent unwanted drain from the battery 26 in the event of that V1 becomes excessively low for some reason—for example, because of a short circuit in the front end circuitry 149. Diode 122 in such a circumstance would prevent Vbat from draining through (in particular) the normal charging path to be described subsequently.

Figure 5A:
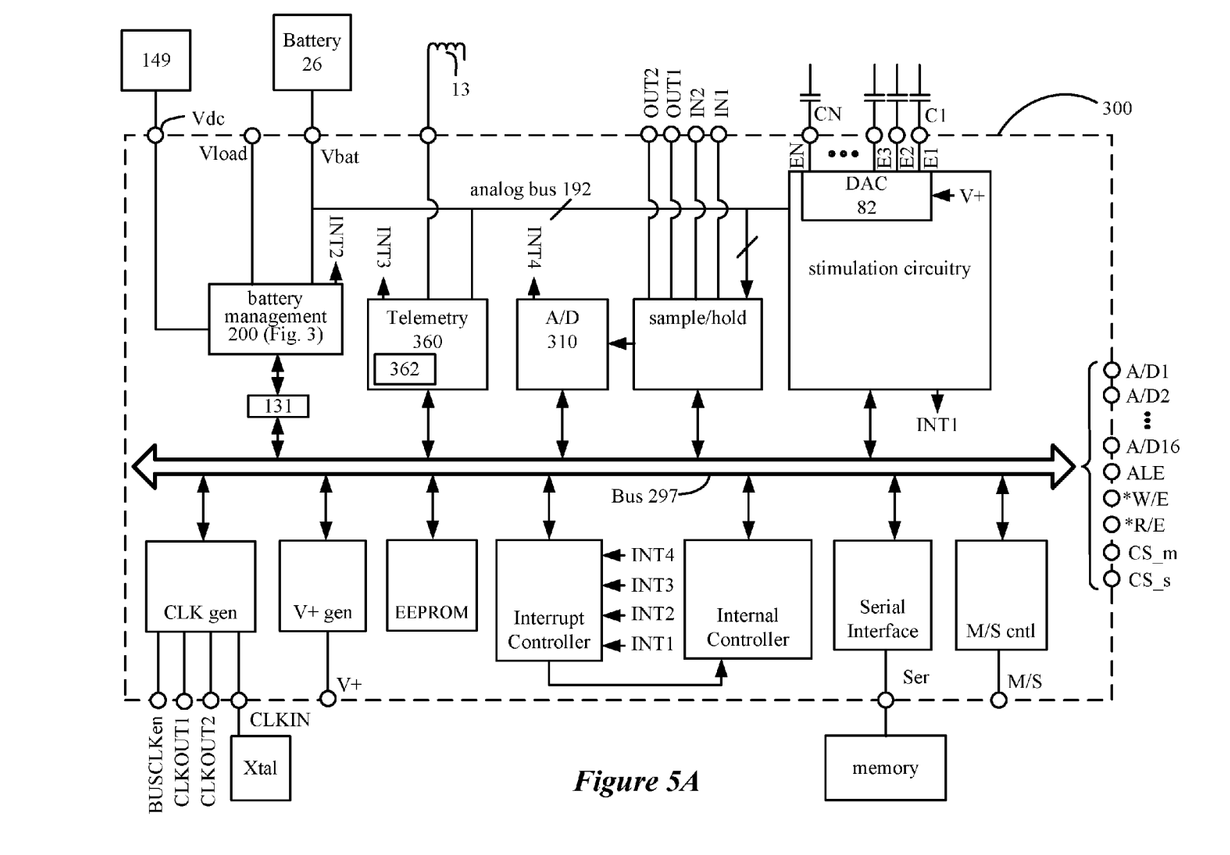
FIGS. 5A and 5B shows one implementation of the improved battery management circuitry as implemented in an integrated circuit and as coupled to other components in the IPG.
Figure 5B:
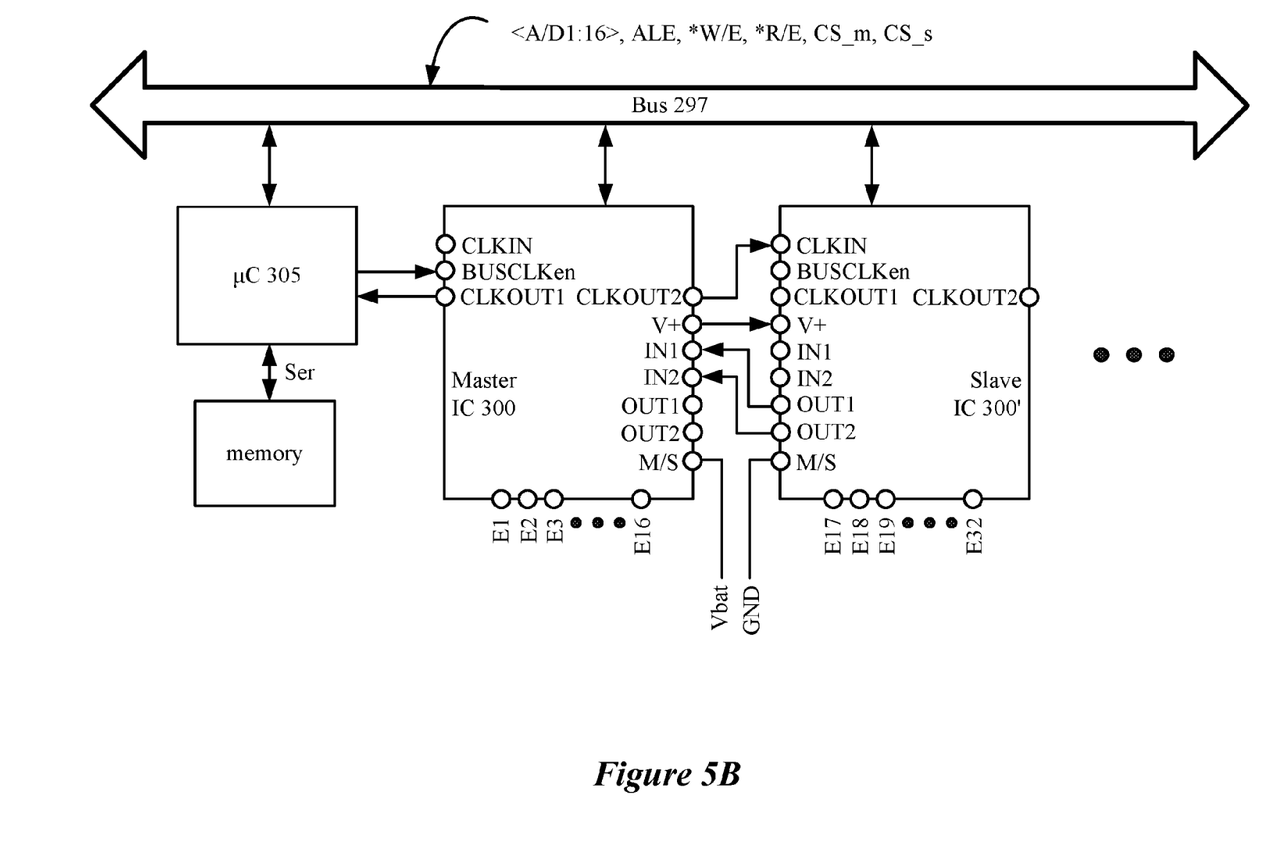

Although implementable in many ways, in one embodiment, the front end circuitry 149 and the battery 26 preferably comprise discrete off-chip components, while the battery management circuitry 200 is included on an integrated circuit (IC) 300, shown in FIG. 5A. IC 300 can comprise other circuit blocks performing other functions within the implantable medical device. Most all of these circuit blocks are ultimately powered by the battery 26 via the load isolation circuitry 155, and hence comprise part of the generic load 160 referred to above. Additionally, IC 300 may itself be coupled to other components within the IPG 100, such as a microcontroller 305, as shown in FIG. 5B, which microcontroller 305 and other components are also powered by the battery 26, and hence comprise part of the load 160. The various circuit blocks in the IC 300, and external components, can be coupled by a bus 297 to allow them to communicate. The bus 297 comprises various bus signals (address/data, write/read enable, addles latch enable, etc.) which operate on the bus 297 in accordance with a protocol. Because IC 300, its various circuits blocks, the microcontroller 305, bus 297, the bus communication protocol, and other details from FIGS. 5A and 5B are described in U.S. Patent Application Publication 2012/0095529, incorporated herein by reference in its entirety, further details concerning these Figures are not belabored here. Microcontroller 305 could also be integrated on the same IC 300 that includes the battery management circuitry 200. In an actual implementation, load 160 includes one or more voltage regulators for producing power supply voltages for the various blocks and components in the IPG 100.

At Vdc, circuitry 200 splits into a normal charging path and a trickle charging path. The trickle charging path is passive, i.e., is not gated and requires no other power than that provided by the magnetic charging field. The trickle path proceeds from node Vdc to the battery 26 through a current-limiting resistor 124 and one or more diodes 126. The trickle charging path is used to provide a small charging current, Itrickle, to the battery 26 when the voltage of the battery, Vbat, is lower than the minimum voltage required for normal circuit operation (e.g., less than 2.5 Volts). Specifically, to produce a trickle charge current, Vdc must be higher than the sum of the voltage drop across the diode(s) 126 and the voltage of the battery 26, Vbat. Under typical conditions and assuming three diodes 126 and a 200-ohm resistor 124 are used, the drop across the resistor 124 and diode(s) 126 will be about 2.0 Volts (which magnitude can be adjusted by changing the resistance or the number of diodes). Therefore, a trickle charging current will passively flow into the battery if Vdc is greater than about 2.0V+Vbat. If this condition is not met, indicating either that Vdc is sufficiently small or that Vbat is sufficiently high, the diodes 126 will be reversed biased, and will prevent the battery 26 from draining backwards through the trickle charging path.

Because it is passive, the trickle charging path can produce a trickle charging current even if the battery 26 is being charged through the normal charging path (which is described further below). However, because Itrickle (usually on the order of a few milliamps) would typical be very small compared to Inormal (usually on the order of tens of milliamps), such additional charging current would be insignificant by comparison.

The normal charging path proceeds from Vdc to the battery 26 through current/voltage source 130 (explained in further detail later with respect to FIG. 6), a charging current sense resistor 132, and an overvoltage protection switch 136. The charging current sense resistor 132 is relatively small (e.g., 1 ohm), and the voltage drop across this resistor is monitored by a charging current detection circuit 134. Charging current detection circuit 134 can comprise a differential amplifier for producing an analog voltage output, CI, indicative of the charging current, Inormal. This analog output, CI, can be digitized using an Analog-to-Digital (A/D) Converter 310 (see FIG. 5A), and used by the controller circuitry in the IPG for any useful purpose. For example, CI can be logged in the IPG 100 to provide a historical record of charging performance. CI can also be telemetered to the external charger 50 for use in adjusting (or terminating) the magnetic charging field produced by the external controller, or for assisting the external charger 50 in aligning the magnetic field to the IPG. See, e.g., U.S. Pat. Nos. 8,744,592; 8,676,318; 8,994,325; and U.S. Patent Application Publication 2011/0276111. Or, CI can be used to control charging directly, for example, by disabling the source 130 should CI exceed a threshold. However, charging circuitry 150 can rely on other safeguards and data beyond CI, and resistor 132 and charge current detector 134 are therefore merely optional in the circuitry.

After passing through the charging current sense resistor 132, the normal charging current, Inormal, proceeds to a PMOS overvoltage protection transistor (switch) 136, which is controlled by an overvoltage control signal, OV. Overvoltage control signal OV comprises a digital signal generated by an overvoltage detector 142, which compares Vbat to a maximum allowed voltage, Vmax1. Vmax1 can be programmed by the designer in many different ways, but in one embodiment is hard-wired using resistors formed in a top-most metallic layer in the IC 300. Vmax1 is also derived from voltage references that are independent from any reference used to charge the battery 26. This passive and independent means for setting Vmax1 is preferred over active calibration signals, because active calibration signals can fail, resulting in an improper (and possibly, unsafe) value for Vmax1. Because Vmax1 is set independently, a failure potentially affecting battery charging should not likewise affect the safety mechanism that Vmax1 provides. In one embodiment, Vmax1 can be approximately 4.5 Volts, which can be defined by the particular battery chemistry used.

If Vbat>Vmax1, the OV fault condition is asserted high, which shuts off the switch 136. Such an overvoltage condition suggests that the battery 26 has been adequately charged, and that further charging through the normal charging path is not desired. Opening switch 136 is desired to protect the battery 26 from damage resulting from overcharging. In addition to opening switch 136, OV is also used to activate discharge circuitry 144, which acts to intentionally drain the battery 26, and which is described in further detail later. If Vbat<Vmax1, OV is low, and switch 136 is closed, which allows charging of the battery 26 through the normal charging path to continue.

Connected between the normal and trickle charging paths are diode(s) 128. In a preferred implementation, the number of diodes 128 equals the number of diodes 126 appearing in the trickle charging path. Diode(s) 128 helps to ensure that there is no leakage from the battery 26, particularly when Vbat is already low (e.g., less than 1.0V). When Vbat is low, it can be difficult to provide suitably high voltages to the gate of P-channel transistors 136 to turn it off, and thus this transistors may be in an indeterminate state. By connecting diode(s) 126 and 128 at their positive terminals, connecting their negative terminals to either side of the overvoltage switch, an ensuring the same number of diodes, this arrangement ensures that the potential on the source and drain of switch 136 are the same. This prevents the flow of current through this switch, and therefore inadvertent draining of the battery at low voltages.

As noted earlier, the isolation circuitry 155 intervenes between the positive terminal of the battery 26 (Vbat) and the load 160 powered by the battery 26. As noted earlier, load 160 can comprise any active circuitry in the IPG 100, such as the regulators and other circuit blocks in the IC 300, the microcontroller 305, or other components. Vload in effect comprises a power supply voltage to be used by such components.

In the example shown, isolation circuitry 155 comprises two P-channel transistors (switches) 152 and 154 wired in parallel. The two transistors 152 and 154 are preferably sized differently to change the resistance across them, i.e., the resistance from the battery 26 to the load 160. Either or both of switches 152 and 154 can be closed to provide power from the battery 26 to the load, regardless of whether the battery 26 is currently being charged, subject to their control as discussed further below. Switches 152 and 154 would generally both be closed during normal operation of the IPG 100 when battery charging is not taking place, again subject to the control discussed below.

Spanning the switches 152 and 154 is an overcurrent detector 156. The overcurrent detector 156 assesses the load current, Iload, flowing between the battery 26 and the load 160, and asserts a digital overcurrent control fault condition signal, OI, when the Iload is above a threshold, Imax. As with Vmax1 used by the overvoltage detector 142, Imax can be programmed in many different ways, but in a preferred embodiment is set using metallic resistors as described earlier. One skilled in the art will understand that the overcurrent detector 156 infers Iload by sensing a difference in voltage on both sides of the switches 152 and 154, and then dividing this difference by the known values of the resistance of the switches. (This resistance will vary depending whether switch 152, 154, or both are closed, but this is known and compensated for by the system). Imax in one embodiment can comprise 400 mA.

Figure 4A:
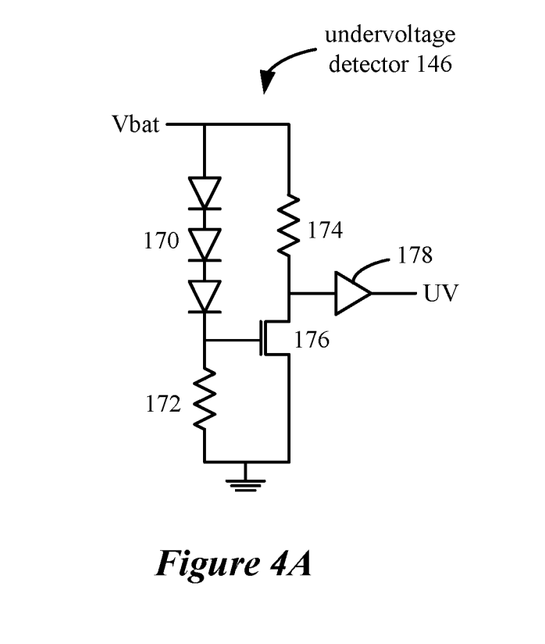
FIGS. 4A and 4B show details of some of the circuits in the improved battery management circuitry.

Switch 152 in the isolation circuitry 155 is of relatively high resistance (e.g., approximately 100 ohms), and is gated by a digital undervoltage control fault condition signal UV. The undervoltage control signal UV is generated by an undervoltage detector 146, which is shown in further detail in FIG. 4A. Note that the undervoltage detector 146 is acts passively (i.e., doesn't require any control signals) to output UV, which is preferred because this circuit must work reliably at low battery voltage levels. The undervoltage detector 146 asserts the undervoltage control signal UV high when Vbat is below a threshold, Vmin, which can be approximately 1.8 Volts. Normally, when Vbat is suitably high, the voltage divider formed by diodes 170 and 10 Mohm resistor 172 forms a suitably high voltage at the gate of N-channel transistor 176 to turn it on. This pulls UV to ground (low) through buffer 178. Because switch 152 comprises a P-channel transistor, this low value for UV closes the switch 152, which couples the battery 26 to the load 160. By contrast, when Vbat is low (e.g., below 1.8V), the voltage at the input of the N-channel transistor 176 is not high enough to turn on that transistor. UV thus floats to the approximate level of Vbat through a 20 Mohm resistor 174, and is therefore high. Asserting UV high opens switch 152, which decouples the battery 26 from the load 160. To summarize, the undervoltage detector 146 causes switch 152 to close when Vbat>Vmin, but opens switch 152 when Vbat<Vmin to keep the load 160 from further draining the already-low battery 26. This is particularly useful if the IPG 100 has been put in storage (or a specific storage mode) to keep the battery from quickly depleting.

Referring again to FIG. 3, switch 154 in the isolation circuitry 155 is of relatively low resistance (e.g., 0.5 ohms) and is gated by a reset signal, RST. RST is formed by an OR gate 153, which receives the undervoltage control signal UV, the overcurrent control signal OI, and a digital control fault condition signal μ from a Reed Switch 151. Reed switches 151 are known in the art of implantable medical devices, and are used to shut down the IPG 100 in an emergency when a patient or clinician externally positions an emergency shut-down magnet proximate to the IPG 100. Further details concerning the operation of a Reed switch 151 can be found for example in U.S. Pat. No. 8,473,070. By virtue of the OR gate 153, assertion of any of fault conditions μ, UV, or OI will cause RST to go high, which will turn off the P-channel switch 154.

Switches 152 and 154 work together to selectively decouple the battery 26 from the load 160 depending on a particular condition being experienced. In the event of an undervoltage condition (when Vbat<Vmin and UV is asserted), both of switches 152 and 154 are opened to isolate the battery 26 from the load 160 and to keep the load 160 from further draining the already-low battery 26.

By contrast, if an overcurrent condition exists (oI is asserted) or if the Reed switch 151 has been activated (μ is asserted), but there is no undervoltage condition (UV is not asserted), there are legitimate concerns suggesting that the battery 26 should be decoupled from the load 160. For example, if OI is asserted, the load 160 is draining too much current, which may too quickly drain the battery 26, and which may cause the IPG 100 to heat to unsafe levels. If μ is asserted, the patient is experiencing some sort of unknown problem, which again may indicate that the battery should be decoupled to effectively power down the IPG 100.

Despite the concerns raised by assertion of OI or μ, it is still desirable to maintain some degree of coupling between the battery 26 and the load 160 so that the digital circuitry in the IPG 100, such as the microcontroller 305 (FIG. 5B), is still capable of functioning and dealing with the condition in an appropriate manner. For example, if OI is asserted, diagnostic circuitry in the IPG 100 will require power to assess, and perhaps remedy, the cause of the excessive load current, Iload. If μ is asserted, it may still be necessary to keep the IPG 100 powered for at least a short time so that the IPG can be shut down in an orderly fashion, a point addressed in the above-referenced '070 Patent. In either case, some power may be needed to allow the microcontroller 305 in the IPG 100 to release the reset, RST, which is otherwise latched.

Although low-resistance switch 154 is opened upon the occurrence of these conditions, high-resistance switch 152 is still closed (again, assuming that an undervoltage condition, UV, does not exist). This provides a relatively high-resistance coupling between the battery 26 and the load 160. This limits Iload, but still provides enough power to keep the digital circuitry in the IPG 100 conscious to perform basic functions, in particular those related to dealing with, and perhaps releasing, the reset condition, RST.

Figure 4B:
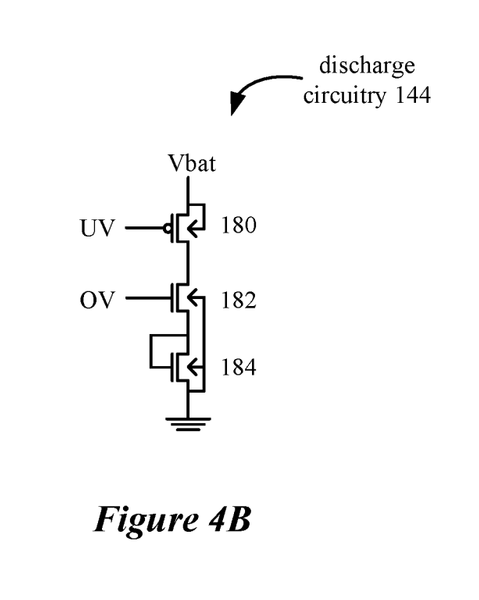

As noted earlier, discharge circuitry 144 acts to controllably discharge the battery 26 during an overvoltage condition. The discharge circuitry 144 is shown in detail in FIG. 4B, and comprises a controllable resistance to ground formed of transistors. A P-channel transistor 180 is gated by the undervoltage signal UV, and an N-channel transistor 182 is gated by the overvoltage signal OV. Transistor 184 is wired as a MOS diode with its gate connected to its drain. When OV is asserted (i.e., when Vbat>Vmax1), transistors 182 and 184 conduct. Because there is no undervoltage condition, UV will not be asserted, which will also cause P-channel transistor 180 to conduct, thus creating a resistance between Vbat and ground to bleed charge from the battery. Discharge circuitry 144 when active in this fashion will draw more current than will the trickle charge path, which is important because the passive trickle charge path cannot be turned off. If the discharge circuitry 144 did not draw such a relatively high current compared to the trickle charge path, Vbat could continue to increase despite the effort to discharge. When active to couple Vbat to ground, the resistance through the transistors 180, 182, and 184 is approximately 200 ohms. The diode-connected transistor 184 creates a reasonably well-known voltage at the drain of OV transistor 182. The OV signal is regulated and thus Vgs of 182 is determined by the drop over 184, thereby creating a feedback mechanism that to some degree regulates the discharge current. Although the discharge circuitry 144 need not activate during an undervoltage condition (i.e., when Vbat<Vmin), it still receives the undervoltage signal UV to ensure that the discharge circuitry is off and will not inadvertently drain the battery 26 during an undervoltage condition: during an undervoltage condition, UV is asserted high, which will turn of transistor 180, ensuring that Vbat is decoupled from ground.

Figure 6:
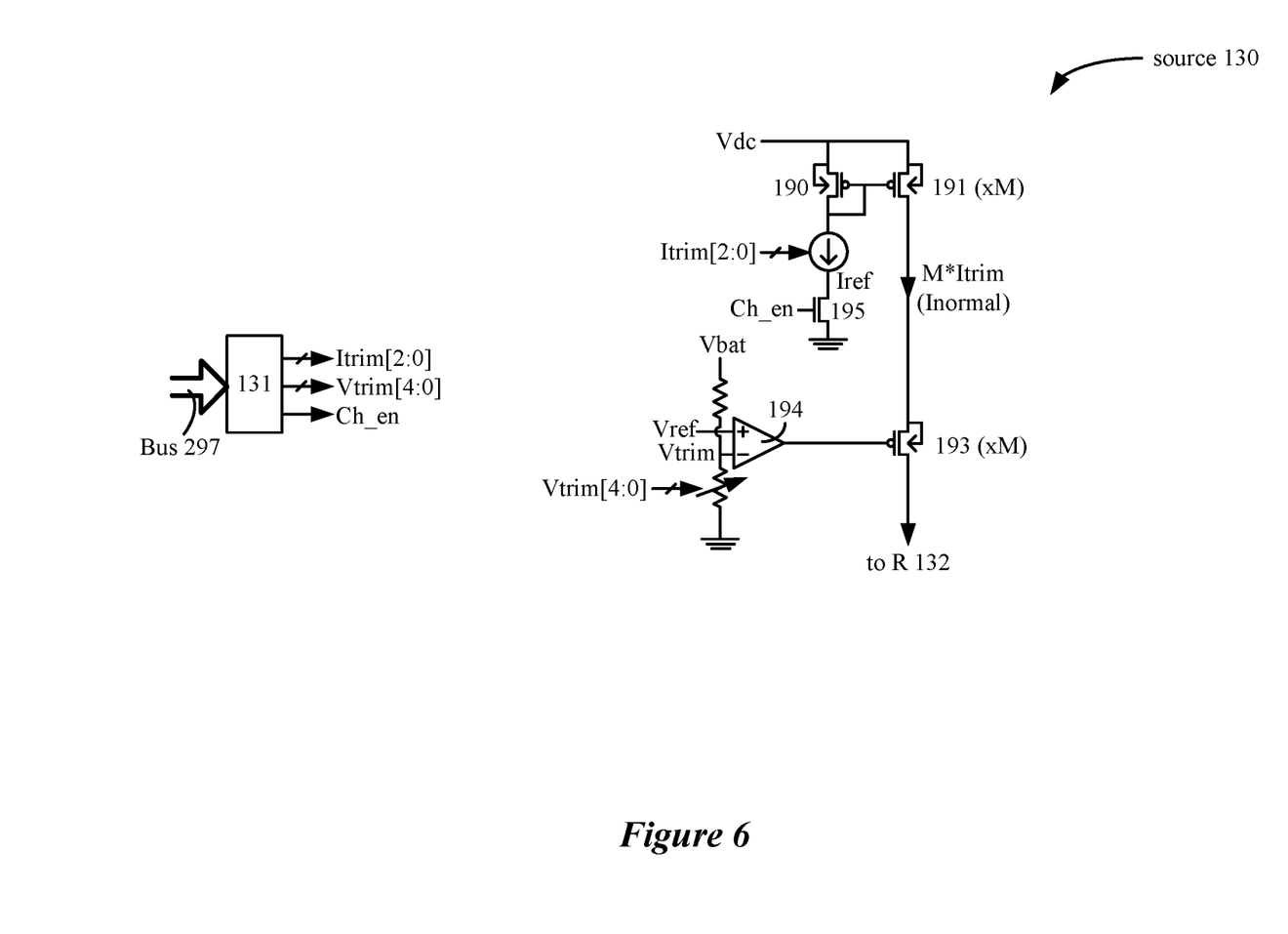
FIG. 6 shows a simplified circuit representing the current/voltage source used in the improved battery management circuitry.

FIG. 6 shows the current/voltage source circuitry 130 in the normal charging path in further detail. As its name indicates, source 130 can provide either a constant current or a constant voltage to the battery 26 during charging, as will be explained momentarily. Vdc (see FIG. 3) comprises the power supply for the source 130, and feeds a current mirror comprised of P-channel transistors 190 and 191. Reference transistor 190 is provided with a programmable current Itrim, which is set by three control signals Itrim[2:0] provided by a source controller 131. The source controller 131 resides within the battery management circuitry block 200, and receives the bus signals 297 referred to earlier. In this way, the microcontroller 305 can control the source controller 131 to provide appropriate control signals to the source 130. Transistors 191 preferably comprises a network of M parallel-wired transistors, thus operating to amplify Itrim to a magnitude of M*Itrim in the normal charging path. In one example, M can equal 500.

Vbat is assessed during charging using an amplifier 194, which is used to convert operation of the source 130 from constant current charging to constant voltage charging of the battery 26 when Vbat exceeds a threshold, Vt, which may be 4.0V or so. A reference voltage Vref is provided to the non-inverting input of the amplifier 194, while a voltage-divided version of Vbat (Vtrim) is provided to the inverting input. Vtrim is trimmable using a variable resistor controlled by five signals Vtrim[4:0], which like Itrim[2:0] are output by the source controller 131. In effect Vtrim[4:0] adjusts the threshold value Vt of the switching point between constant current and constant voltage charging. When Vtrim<Vref, indicating that Vbat<Vt, the amplifier 194 turns off P-channel transistor 193. Despite this, current still flows through transistor 193 by virtue of the current mirror, and the battery 26 is changed at a constant current of approximately M*Itrim.

When Vtrim>Vref, indicating that Vbat>Vt, the amplifier 194 starts to turn on transistor 193. However, as Vbat increases during charging, the source of transistor 193 also increases. This lessens the gate-to-source voltage of transistor 193 over time, and tends over time to shut off that transistor. In effect, under these conditions, the current is limited by the battery's impedance, and transistor 193 essentially provides a constant voltage to charge the battery rather than a constant current. When subjected to constant voltage, the current through the path will exponentially decrease over time.

The source 130 is enabled by a charge enable signal (Ch_en), which is asserted high by the source controller 131 when conditions are suitable to allow for either constant current or constant voltage charging of the battery 26. When enabled, N-channel transistor 195 is turned on, which allows the reference current Itrim to flow. When disabled, transistor 195 is off. Thus, when Ch_en is low, no current is allowed to flow through the normal charging path (Inormal=0), effectively disabling the source 130 from charging the battery 26.

Figure 7:
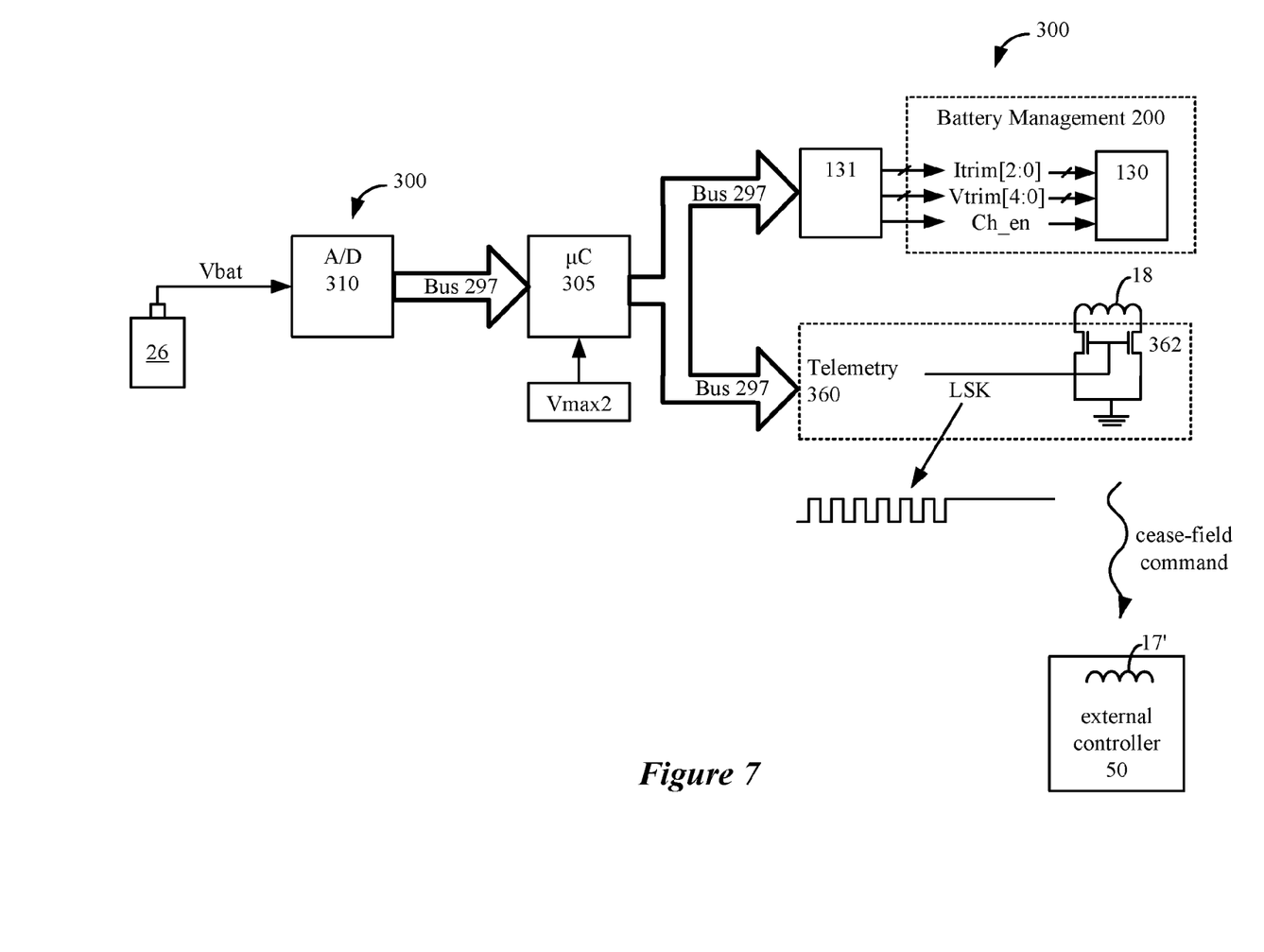
FIG. 7 shows the operation of firmware in the IPG for controlling the source of FIG. 6, and for controlling other aspects to prevent overcharging of the battery.

FIG. 7 shows how the firmware of the IPG 100 can be used to provide further control and protection from overcharging, and in particular shows how such firmware can control the operation of the current/voltage source 130 of FIG. 6. In FIG. 7, a second maximum voltage, Vmax2, for the battery voltage Vbat is used to provide overvoltage protection. Such control is in addition to the hardware control provided by Vmax1 to open switch 136 (FIG. 3) during an overvoltage condition (oV) as explained earlier. Thus, in a preferred IPG 100, two maximum battery voltages are used to provide control and protection during charging: Vmax1 provides isolation for the battery, while Vmax2 provides other means of control as will now be explained.

FIG. 7 shows the flow of data through the circuitry in the IPG 100 from left to right as relevant to overvoltage control. The battery voltage Vbat is first digitized by A/D block 310 in the IC 300 (see FIG. 5A), and that digitized value is then sent by bus 297 to the microcontroller 305. The value for Vmax2 has already been programmed into the IPG 100 circuitry, and is accessible to the microcontroller 305 as shown. In this regard, Vmax2 can be programmed into memory within the microcontroller itself, or can reside in a register outside of the microcontroller, for example in an EEPROM coupled to the bus 297 (FIG. 5A). Regardless, the microcontroller 305 compares Vbat to Vmax2, and issues appropriate commands back to the IC 300 via bus 297 in response. In particular, commands are sent to the source controller 131 for the source 130 within the battery management block 200, and to the LSK switches 362 in the telemetry block 360.

When Vbat<Vmax2, no overvoltage condition is understood, and charging occurs normally. The source 130 is enabled, i.e., Ch_en=1, which as explained earlier with reference to FIG. 6, allows the source 130 to provide either constant current or constant voltage charging to the battery 26.

If the microcontroller 305 determines that Vbat>Vmax2, appropriate measure are taken to protect the battery 26 and ensure that it is not further programmed. In this circumstance, the source 130 is disabled, i.e., Ch_en is set to 0, which prevents the source 130 from providing any current to the battery 26.

Additionally, signal LSK is triggered to send a cease-field command to the external charger 50 to cease production of the magnetic charging field. This signal LSK can comprise an alternating signal (010101 . . . ) that is asserted for a fixed time (e.g., ten seconds). The LSK signal toggles transistors 362, which causes the ends of the charging coil 18 to toggle to ground. This changes the mutual inductance between the charging coil 18 in the IPG 100 and charging coil 17' in the external charger 50, which in effect produces reflections detectable at the external charger 50. When these reflections are received, the external charger 50 can cease production of the magnetic charging field, thus protecting the battery 26 from overcharging further.

After the fixed time for the alternating signal, and as a further protective measure, signal LSK can be asserted high for another fixed period of time (e.g., five minutes). This works to nullify the magnetic charging field at the IPG 100 in case the cease-field command was not received and acted upon by the external charger 50. Asserting LSK high turns on transistors 362, and grounding both ends of the IPG's charging coil 18. With both ends of the charging coil 18 grounded, no DC voltage can be produced by the front end 149 of the charging circuitry, i.e., Vdc should equal 0 even if a magnetic charging field is being provided by the external charger 50. Without such a DC potential, neither the normal nor trickle charging paths can provide current to the battery 26.

In another embodiment, the value for Vbat can also be telemetered to the external charger 50 via Load Shift Keying so that the external charger 50 can take appropriate steps during charging. For example, if Vbat is particularly low, the external charger 50 may increase the strength of the magnetic charging field to speed up the charging process. The external charger 50 can also cease production of the magnetic charging field when Vbat approaches a suitable large value. For example, the external charger 50 may be programmed with a threshold, Vmax3. When Vbat as telemetered from the IPG 100 exceeds Vmax3, the external charger 50 can suspend production of the magnetic charging field as yet another means of ensuring that the battery 26 does not become overcharged.

Figure 8:
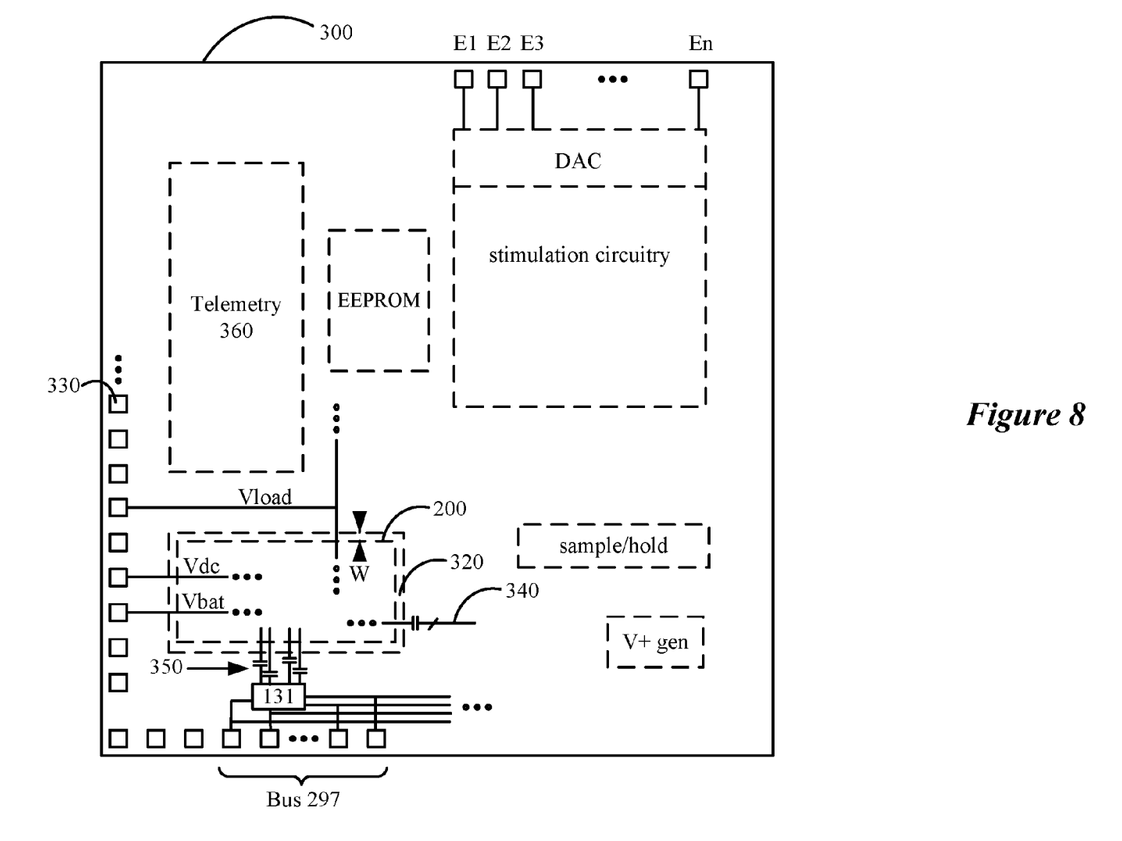
FIG. 8 shows a layout of an integrated circuit including placement of the improved battery management circuitry.

FIG. 8 shows a plan view of IC 300, and shows the placement of the battery management circuitry 200 relative to just a few other circuit blocks. Battery management circuitry 200 is provided a dedicated area on the IC 300, and protective measures are taken to improve battery management circuit 200 reliability. Such protective measures generally isolate the battery management circuitry 200 from the remainder of the circuitry on the IC 300, with the goal that reliability problems elsewhere on the IC 300 are less likely to produce reliability problems in the battery management circuitry 200.

First, signaling into and out of the battery management circuitry 200 is kept to a minimum. As shown, Vdc and Vbat (as discussed earlier with reference to FIG. 3) enter battery management circuitry 200 from IC bond pads 330. One skilled in the art will understand that bond pads 330 provide contact points for electrically connecting the IC 300 to other discrete components or integrated circuits in the IPG 100. Vload exits battery management circuitry 200, and as noted earlier, provides the power supply for the remainder of the circuit blocks on the IC 300, as well as other circuitry outside the IC 300, such as the microcontroller 305 (FIG. 5B). As such, Vload is disseminated within IC 300 and is also ported outside the IC 300 via its own bond pad 330.

Also porting into battery management circuitry 200 are signals 350 derived by the source controller 131, such as Itrim, Vtrim, and Ch_en (see FIG. 6). Other signals 340 may also port into and out of the battery management circuitry 200, such as various interrupt signals indicative of the various over- and under-voltage or current conditions described earlier. Signals 340 and 350 porting in and out of the battery management circuitry block 200 preferably do so at the top level of metal used in the formation of the IC 300 to maximize their insulation with respect to the underlying IC substrate, but this is not strictly necessary.

A second protective measure used with battery management circuitry 200 comprises prevention of DC coupling of signals 340 and 350 into and out of the block. As shown, decoupling capacitors are used with all signals that flow into or out of battery management circuitry block 200. That is, signals in and out of the block are AC coupled (i.e., galvanically isolated), and there is thus no DC connection between the battery management block 200 and circuitry outside this block, which is desired to keep failures from outside from unsafely affecting operation within the block. For example, a failure outside the block 200 will be unable to inject DC current into the block 200 through the signal paths. This improves the reliability of the block 200, and is particularly important when one considers the importance of controlling DC current flow within the block. Although such AC coupling of signals is shown by the use of discrete capacitors, such capacitances may also comprise other structures, such as the insulative gates of MOS transistors. Thus, level shifters for example, which employ such insulated gates, can be used in lieu of discrete capacitors.

A third protective measure designed to isolate battery management circuitry 200 is the use of an isolation area 320 in the substrate of the IC 300. The isolation area 320 comprises a ring of isolation around the battery management circuitry 200 of a given width, W, which may be at least an order of magnitude larger than the smallest line width used in the fabrication of IC 300. No active structures are formed in the IC substrate underlying isolation area 320. Width W provides a much larger than normal physical spacing between the battery management block 200 and surrounding circuitry, i.e., a much larger physical spacing than IC design rules would otherwise indicate between different circuit blocks. Such physical spacing is particular preferred to prevent mechanical damage to other portions of the IC (e.g., cracks) from adversely affecting the battery management block 200.

It should be noted that battery management circuitry 200 could also comprise its own integrated circuit separate from, but coupled to IC 300. Separating the two would allay some of the above concerns about the reliability of the IC 300 affecting operation of the battery management circuitry 200. However, it is preferred for integration to include the battery management circuitry 200 on the IC 300, and to employ the protective measures just discussed. Additionally, semiconductor processes with truly isolated areas such as SOI (Silicon On Insulator) can effectively allow complete separation even on the same integrated circuit.

While this disclosure has provided several different protective measures by which charging of a battery in a medical implant can be performed or implemented, it should be realized that not all such measures need be taken in a given application. Which measures are taken will depend on designer choices, and on desired levels of redundant protection.

"Diode" as used herein should be understood as comprising any device capable of limiting the flow of current in one direction, and can include transistors wired to act like traditional diodes (e.g., a MOSFET with it gate connected to one of the source or drain, or a BJT transistor with its base connected to one of the collector or emitter), or any other suitable rectifying device.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Circuitry for an implantable medical device, comprising:
   charging circuitry for providing power to a battery terminal node;
   isolation circuitry comprising first and second load switches in parallel, wherein both of the first and second load switches are directly connected to the battery terminal node and to a load voltage; and
   active circuitry within the implantable medical device, wherein the load voltage comprises a power supply voltage for the active circuitry,
   wherein the first load switch is opened if a voltage at the battery terminal node falls below a threshold, and
   wherein the second load switch is opened if at least one other fault condition is asserted.

2. The circuitry of claim 1, wherein the first load switch has a first resistance, and the second load switch has a second resistance smaller than the first resistance.

3. The circuitry of claim 1,
   wherein the second load switch is also opened if the voltage at the battery terminal node falls below the threshold.

4. The circuitry of claim 3, wherein the first load switch has a first resistance, and the second load switch has a second resistance smaller than the first resistance.

5. The circuitry of claim 1, wherein the at least one other fault condition comprises an overcurrent between the battery terminal node and the load.

6. The circuitry of claim 1, wherein the at least one other fault conditions comprise an overcurrent between the battery terminal node and the load and an emergency shutdown condition.

7. The circuitry of claim 6, wherein the emergency shutdown condition comprises a magnetic field generated external to the implantable medical device.

8. The circuitry of claim 1, wherein the active circuitry comprises stimulation circuitry configured to provide stimulation to a plurality of electrodes of the implantable medical device.

9. The circuitry of claim 1, wherein the active circuitry comprises one or more voltage regulators for producing power supply voltages for other circuitry in the implantable medical device.

10. Circuitry for an implantable medical device, comprising:
    charging circuitry for providing power to a battery terminal node;
    isolation circuitry comprising a plurality of load switches coupled in parallel between the battery terminal node and a load voltage;
    isolation circuitry comprising a plurality of load switches in parallel, wherein the plurality of load switches are directly connected to the battery terminal node and to a load voltage;
    active circuitry within the implantable medical device, wherein the load voltage comprises a power supply voltage for the active circuitry;
    an undervoltage detector, wherein the undervoltage detector is configured to assert an undervoltage signal if a voltage at the battery terminal node falls below a first threshold;

an overcurrent detector, wherein the overcurrent detector is configured to assert an overcurrent signal if a current between the battery terminal node and the load exceeds a second threshold; and a magnetic field detector, wherein the magnetic field detector is configured to assert a magnetic field signal upon detection of a magnetic field external to the implantable medical device, wherein the plurality of load switches are controlled by the undervoltage signal, the overcurrent signal, and the magnetic field signal.

11. The circuitry of claim 10, wherein the plurality of load switch switches each have different resistances.

12. The circuitry of claim 11, further comprising an OR gate, wherein the OR gate is configured to receive the undervoltage signal, the overcurrent signal, and the magnetic field signal, and wherein the OR gate is configured to output a reset signal to the second load switch, such that if any of the undervoltage signal, the overcurrent signal, or the magnetic field signal are asserted, the reset signal opens the second load switch.

13. The circuitry of claim 12, wherein only the undervoltage signal controls the first load switch, such that the first load switch is opened if the undervoltage signal is asserted.

14. The circuitry of claim 13, wherein the first load switch has a first resistance, and the second load switch has a second resistance smaller than the first resistance.

15. The circuitry of claim 10, wherein the plurality of load switches comprises a first load switch and a second load switch.

16. The circuitry of claim 10, wherein the active circuitry comprises stimulation circuitry configured to provide stimulation to a plurality of electrodes of the implantable medical device.

17. The circuitry of claim 10, wherein the active circuitry comprises one or more voltage regulators for producing power supply voltages for other circuitry in the implantable medical device.

18. Circuitry for an implantable medical device, comprising:

charging circuitry for providing power to a battery terminal node;

isolation circuitry comprising first and second load switches coupled in parallel between the battery terminal node and a load voltage, wherein the first and second load switches have first terminals that are directly connected, and wherein the first and second switches have second terminals that are directly connected; and active circuitry within the implantable medical device, wherein the load voltage comprises a power supply voltage for the active circuitry, wherein the first load switch is opened if a voltage at the battery terminal node falls below a threshold, and wherein the second load switch is opened if at least one other fault condition is asserted.

19. The circuitry of claim 18, wherein the first terminals are further directly connected to the battery terminal node, and wherein the second terminals are further directly connected to the load voltage.

20. The circuitry of claim 18, wherein the first load switch has a first resistance, and the second load switch has a second resistance smaller than the first resistance.

* * * * *